US011717306B2

(12) United States Patent
Sikora et al.

(10) Patent No.: US 11,717,306 B2
(45) Date of Patent: *Aug. 8, 2023

(54) RETROGRADE RESECTION APPARATUS AND METHOD

(71) Applicant: Arthrosurface Incorporated, Franklin, MA (US)

(72) Inventors: George Sikora, Bridgewater, MA (US); Timothy Brightman, Franklin, MA (US); Steven W. Ek, Bolton, MA (US)

(73) Assignee: Arthrosurface Incorporated, Franklin, MA (US)

( * ) Notice: Subject to any disclaimer, the term of this patent is extended or adjusted under 35 U.S.C. 154(b) by 175 days.

This patent is subject to a terminal disclaimer.

(21) Appl. No.: 17/301,232

(22) Filed: Mar. 30, 2021

(65) Prior Publication Data
US 2022/0047277 A1 Feb. 17, 2022

Related U.S. Application Data

(63) Continuation of application No. 16/101,620, filed on Aug. 13, 2018, now Pat. No. 10,959,740, which is a continuation of application No. 15/153,170, filed on May 12, 2016, now Pat. No. 10,045,788, which is a continuation of application No. 12/001,473, filed on Dec. 11, 2007, now Pat. No. 9,358,029.

(60) Provisional application No. 60/869,404, filed on Dec. 11, 2006.

(51) Int. Cl.
*A61B 17/16* (2006.01)
*A61B 17/32* (2006.01)

(52) U.S. Cl.
CPC ...... *A61B 17/1675* (2013.01); *A61B 17/1617* (2013.01); *A61B 17/32002* (2013.01); *A61B 17/320016* (2013.01)

(58) Field of Classification Search
CPC ............ A61B 17/1617; A61B 17/1675; A61B 17/320016; A61B 17/32002
See application file for complete search history.

(56) References Cited

U.S. PATENT DOCUMENTS

2006/0195112 A1* 8/2006 Ek ...................... A61B 17/1617
606/86 R

* cited by examiner

*Primary Examiner* — Samuel S Hanna
(74) *Attorney, Agent, or Firm* — Goodwin Procter LLP

(57) ABSTRACT

A retrograde resection apparatus may include a cutting blade including a slot defined in the cutting blade, a recess defined in at least a portion of the slot, a screw, including a proximal end and a distal end defining a bore therethrough, a shaft having a distal end and a proximal end, wherein the shaft passes through the bore and the distal end is configured to be received in the recess, and a biasing device configured to bias the shaft against the cutting blade. In addition, the apparatus may include a tether, a first portion of which is affixed to the cutting blade and a second portion of which passes through the bore.

20 Claims, 19 Drawing Sheets

RETROGRADE RESECTION APPARATUS AND METHOD

CROSS-REFERENCE TO RELATED APPLICATIONS

The present application is a continuation of U.S. patent application Ser. No. 16/101,620 (now U.S. Pat. No. 10,959,740), filed Aug. 13, 2018, which is a continuation of U.S. patent application Ser. No. 15/153,170 (now U.S. Pat. No. 10,045,788), filed May 12, 2016, which is a continuation of U.S. patent application Ser. No. 12/001,473 (now U.S. Pat. No. 9,358,029), filed Dec. 11, 2007, which claims the benefit of U.S. Provisional Application No. 60/869,404, filed on Dec. 11, 2006, the disclosures of which are incorporated herein by reference.

FIELD

The present disclosure relates to an apparatus and method for the resection of bone and articular cartilage, for example, for creating an implant site in an articular surface for receiving an articular prosthesis.

BACKGROUND

Articular joints may become damaged as the result of trauma, disease, wear, etc. Advancing damage to an articular joint may result in pain, loss of mobility of the afflicted joint, etc. Various techniques and systems may be used for repairing damaged articular joints in the human body. One common approach for repairing a defective joint is to replace the damaged region with a repair component. Generally a repair component may include a prosthetic device or a biological component.

A critical aspect of a repair procedure is the resection of at least a portion of the damaged articular cartilage and the underlying bone. Often the damaged articular cartilage is resected by opening the joint and directly drilling, cutting, or grinding away the damaged material. Such an approach typically requires at least partial separation of the joint. Separation of the joint necessary for resecting the damaged articular cartilage may result in attendant damage to ligaments and other connective tissues. Damage to the connective tissues of the joint may increase the recovery time, and perhaps limit the ultimate recovery.

BRIEF DESCRIPTION OF THE DRAWINGS

Features and advantages of the invention herein are set forth by way of description of embodiments consistent with the invention. The description of embodiments should be read and understood in conjunction with the accompanying drawings, wherein:

FIG. 18*a* is a perspective view from the top and FIGS. 18*b* and 18*c* are perspective views from the bottom.

DESCRIPTION

Figure 1:
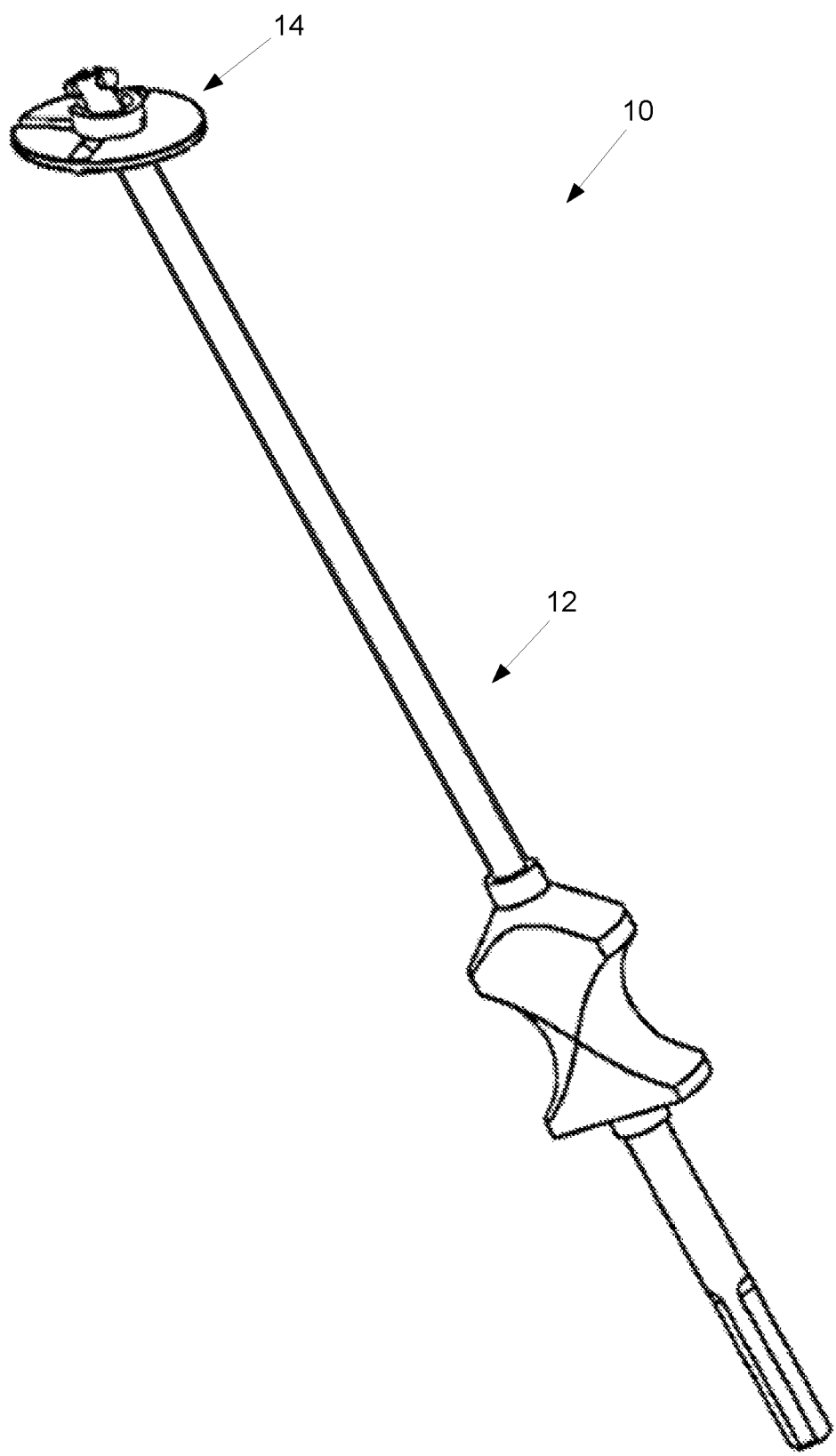
FIG. 1 is a perspective view of a retrograde resection apparatus consistent with the present disclosure.
Figure 2:
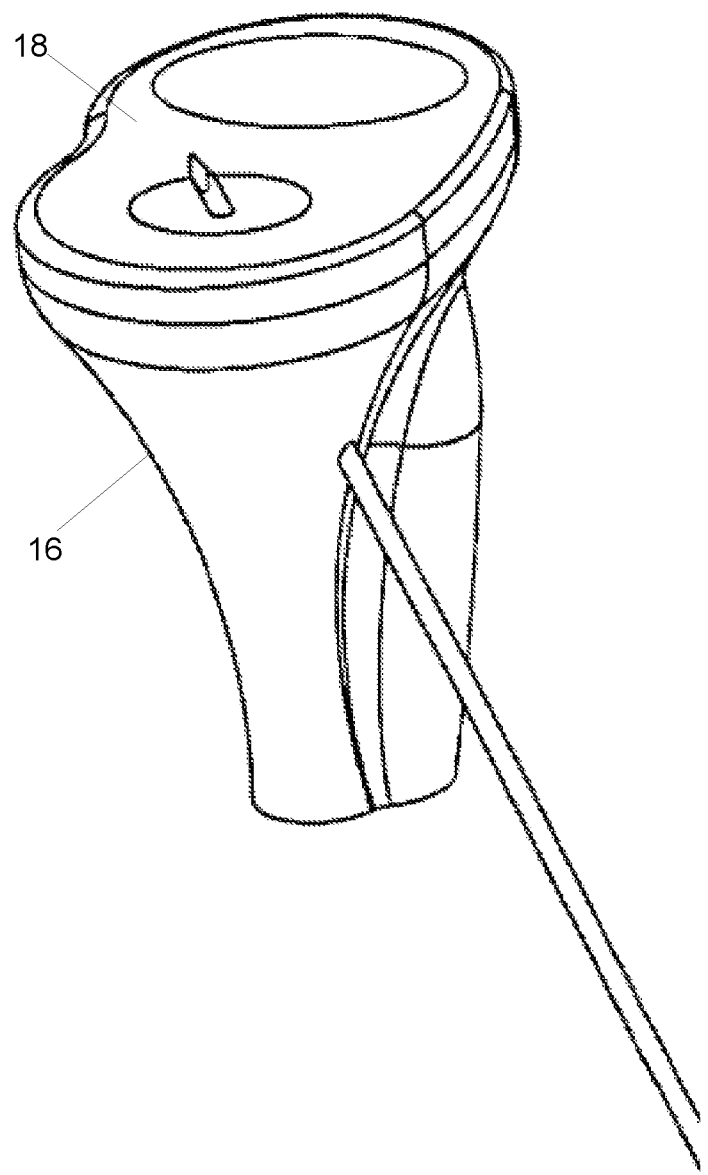
FIG. 2 depicts the use of a retrograde access tunnel in connection with a method for creating an implant site in an articular surface.

A retrograde resection apparatus 10, depicted in FIG. 1, may be used for creating an implant site in an articular surface of a joint by removing at least a portion of the articular surface, which may include at least a portion of the articular cartilage of the joint surface, as well as at least a portion of the bone underlying the articular cartilage. The retrograde resection apparatus 10 may generally include a drive component 12 and a cutting blade 14. The drive component 12 may be coupled to the cutting blade 14 to allow the cutting blade 14 to be rotatably driven relative to the articular surface from a remote site. The drive component 12 may also exert an axial force on the cutting blade 14 to direct and/or control the resection of the articular surface.

In operation, a retrograde access passage may be formed through bone, e.g., the tibia 16 in the illustrated embodiment, behind the target articular surface 18. The retrograde access passage may be created by drilling a hole through a portion of the tibia 16 from a distal position toward the articular surface 18, extending through the bone behind the articular surface 18, as shown in FIG. 1. The opening 22 of the access passage formed in the articular surface 18 may be at, or adjacent to, a desired implant site. The trajectory of the retrograde passage may be controlled in a free-hand manner, or using suitable drill guides, etc. Examples of suitable drill guides and procedures for creating access passages are shown, for example, in U.S. patent application Ser. No. 10/308,718, filed Dec. 3, 2002, in U.S. patent application Ser. No. 11/209,170, filed Aug. 22, 2005, and in U.S. patent application Ser. No. 11/326,133, filed Jan. 5, 2006. The entire disclosures of the foregoing applications are incorporated herein by reference.

Figure 3:
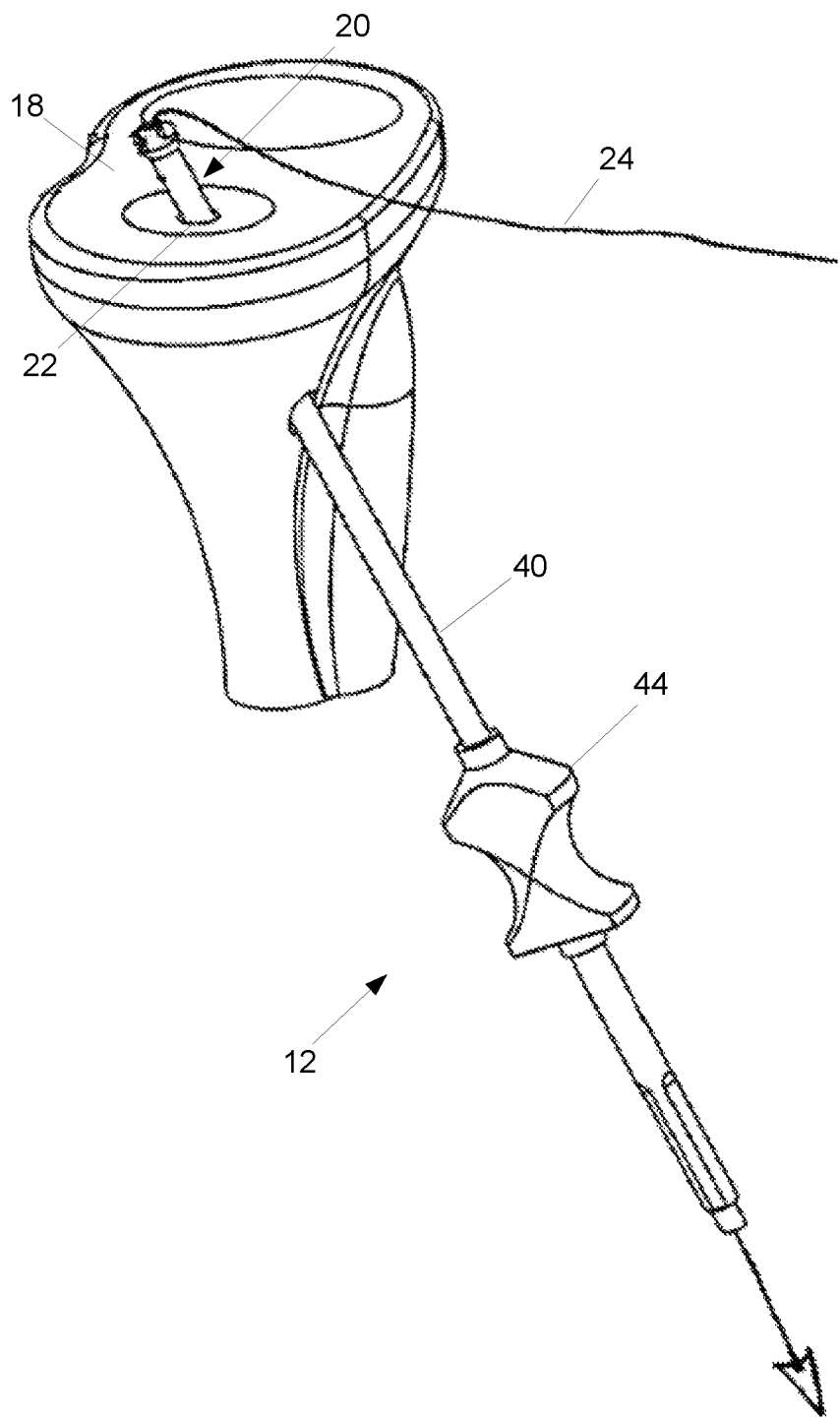
FIG. 3 depicts an initial stage of in situ assembly of the retrograde resection apparatus depicted in FIG. 1.
Figure 4:
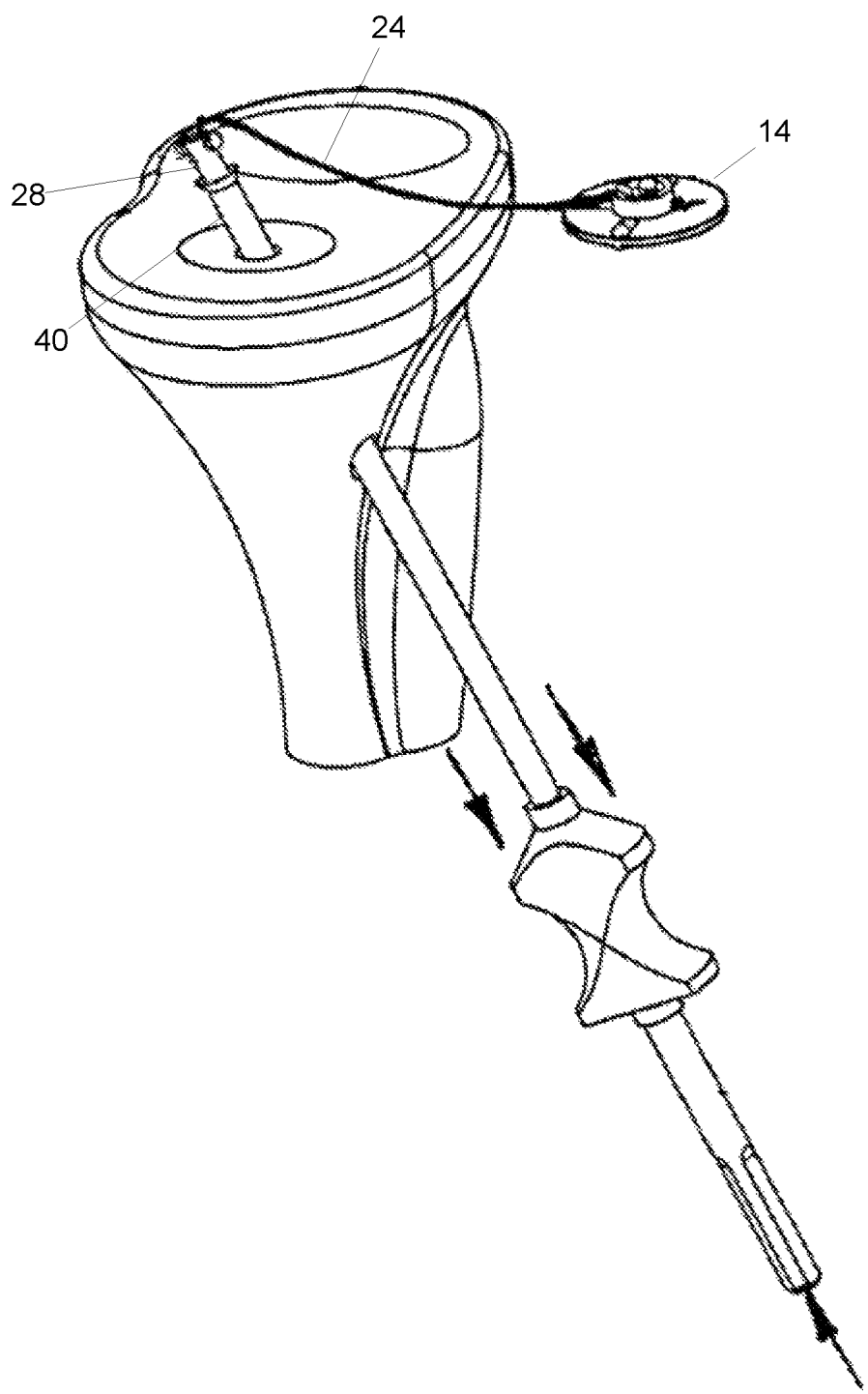
FIG. 4 illustrates a technique for conveying a cutting blade of the retrograde resection apparatus of FIG. 1 into a joint.

As shown in FIGS. 3 and 4, the drive component 12 may be inserted at least partially through the access passage, and the cutting blade 14 may be conveyed to the drive component 12 within the joint. The cutting blade 14 may be generally configured having a thin geometry, such as a disk or wafer. The thin geometry may allow the cutting blade 14 to be introduced into the joint between cooperating articular surfaces with minimal separation of the joint. The relatively small amount of separation between the cooperating articular surfaces of the joint may limit damage to connective tissues of the joint, such as ligaments, etc.

The cutting blade 14 may be conveyed into the joint and to the drive component 12 using a tether 24, such as a flexible wire, cord, etc. The drive component 12 may include a cannulated shaft portion 20, which may be inserted through the access passage so that the distal end of the cannulated shaft portion 20 protrudes above, or is at least adjacent to, the opening 22 of the access passage at the articular surface 18. The tether 24 may be coupled to the cutting blade 14 and the tether 24 may be pulled through the lumen of the cannulated shaft portion 20 of the drive component 12. For example, the tether 24 may be introduced through the drive component 12 into the joint. A suture snare, forceps, etc., may be used capture the tether 24 and draw it from the joint to allow the cutting blade 14 to be attached thereto. Alternatively, the tether 24 may be coupled to the cutting blade 14 and a portion of the tether 24 may be introduced into the joint near the opening 22 of the access passage. The tether 24 may be captured by a suture snare, etc., introduced through the lumen of the shaft portion 20 of the drive component 12, and the tether 24 may be drawn through the drive component 12 to convey the cutting blade 14 to the drive component 12 within the joint.

Figure 5:
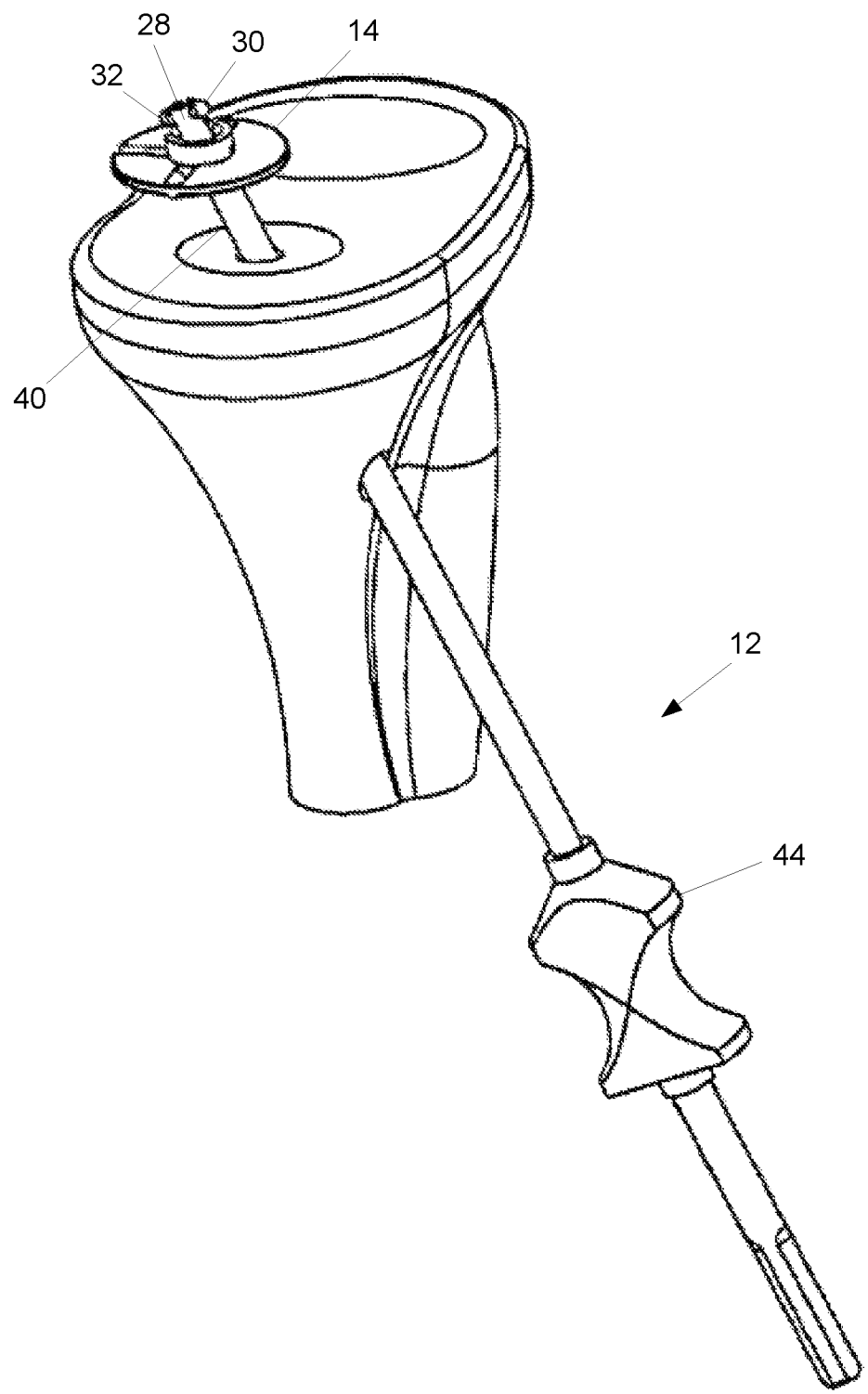
FIG. 5 shows the retrograde resection apparatus of FIG. 1 assembled within a joint.

Once the cutting blade 14 has been conveyed into the joint, the drive component 12 may be drivingly coupled to the cutting blade 14, as shown in FIG. 5. With additional reference to FIGS. 6 and 7, the cutting blade 14 may define a radial slot 26. An inner shaft portion 28 of the drive component 12 may be sized to be received in the slot 26 of the cutting blade 14. The cutting blade 14 may, therefore, be assembled to the drive component 12 by sliding the cutting blade 14 onto the inner shaft portion 28 of the drive component 12.

In an embodiment, rather than conveying the cutting blade to the drive component within the joint using a tether, the cutting blade may be inserted into the joint and installed on the inner shaft portion of the drive component using tweezers, forceps, etc. For example, the cutting blade may be grasped by forceps and inserted into the joint with the slot of the cutting blade oriented to receive the inner shaft portion of the drive component. The cutting blade may be installed on the inner shaft portion and released by the forceps. Various similar techniques may be used for conveying the cutting blade into the joint and assembling the cutting blade to the drive component.

Figure 6:
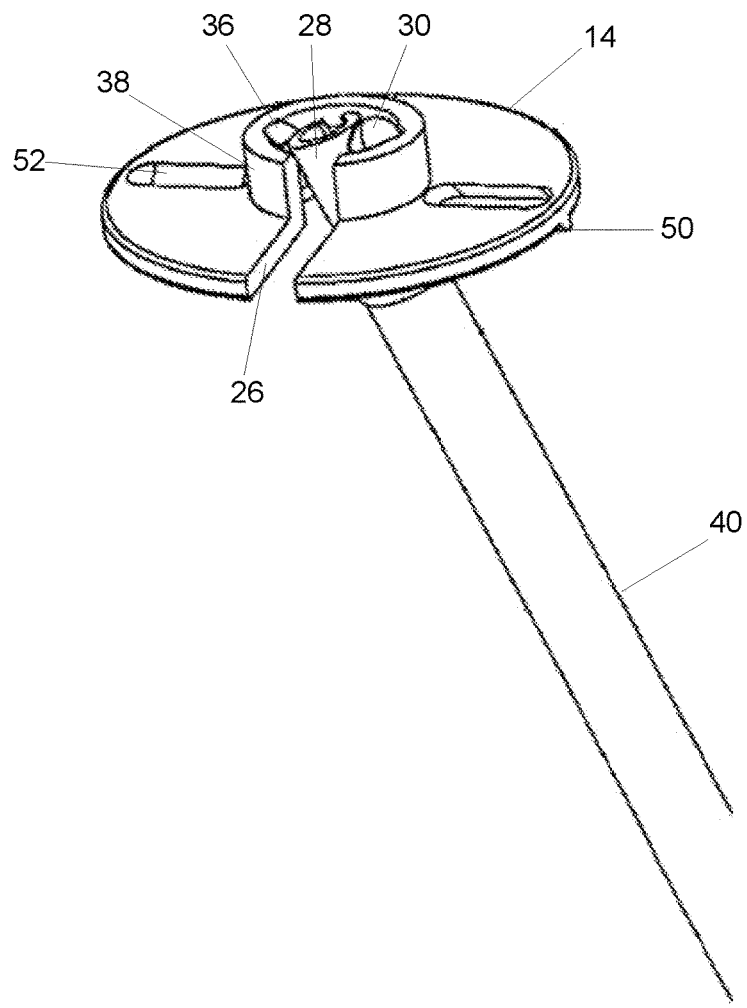
FIG. 6 is a detailed view of the cutting blade assembled to the drive component of the retrograde resection apparatus of FIG. 1.
Figure 7:
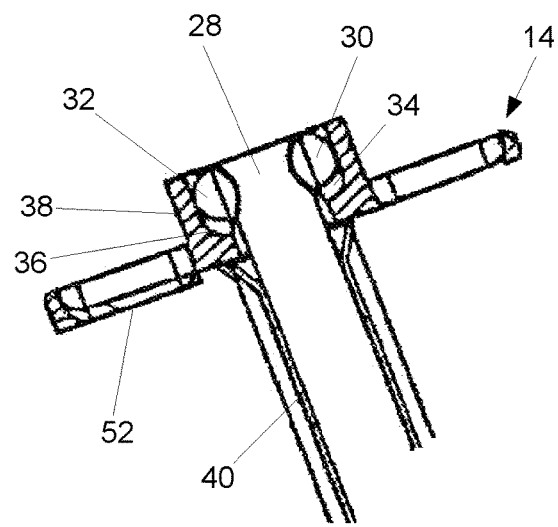
FIG. 7 is a detailed, partial cross-sectional view of the cutting blade and drive component assembly of FIGS. 1 and 6.

The drive component 12 and the cutting blade 14 may include interacting features for transmitting torque from the drive component 12 to the cutting blade 14, e.g., to allow the cutting blade 14 to be rotatably driven by the drive component 12. In the illustrated embodiment, the inner shaft 28 of the drive component 12 may include one or more protrusions 30, 32 which may be received in corresponding recesses 34, 36 in the cutting blade 14. The protrusions 30, 32 may be semi-spherical protrusions, as illustrated, cylindrical members, e.g., in the form of a pin extending radially across the shaft portion, etc. The cutting blade 14 may include a central hub 38, and the recesses 34, 36 may be formed as axially extending slots in the hub 38. As shown in FIGS. 5 through 7, the cutting blade 14 may be slidingly received on the inner shaft portion 28 of the drive component 12 with the protrusions 30, 32 above the hub 38. The protrusions 30, 32 and the recesses 34, 36 may be aligned and the cutting blade 14 and the inner shaft 28 may be moved to engage the protrusions 30, 32 in the recesses 34, 36.

An outer sleeve 40 of the drive component 12 may be slidingly disposed relative to the shaft portion 28. The sleeve 40 may be positioned to engage a bottom surface 42 of the cutting blade 14 and may maintain the engagement of the protrusions 30, 32 in the recesses 34, 36. Additionally, the engagement between the sleeve 40 and the bottom surface 42 of the cutting blade 14 may generally align the cutting blade 14 relative to the drive component 12, e.g., so that the cutting blade 14 is generally perpendicular to the drive component 14. The alignment between the cutting blade and the drive component, however, is not necessary.

The sleeve 40 may be biased toward the distal end of the inner shaft portion 28, e.g., a forward position. The sleeve 40 may be retracted away from the end of the shaft portion 28 to expose at least a portion of the shaft portion 28 to allow the cutting blade 14 to be received on the shaft portion 28 proximal to the protrusions 30, 32. The sleeve 40 may then be urged toward the forward position to urge the drive component 12 into engagement with the cutting blade 14 and to maintain the engagement thereof. For example, a handle 44 may be coupled to the sleeve 40 for sliding the sleeve 40 to a retracted position relative to the shaft portion 28. The sleeve 40 may be biased toward the forward position using any suitable biasing element, e.g., a spring, acting against the sleeve 40, the handle 44, etc. Rather than being biased, or in addition to being biased, the sleeve may be movable between the retraced and the forward positions and may be engaged, or locked, in at least the forward position, if not in both positions.

Figure 8:
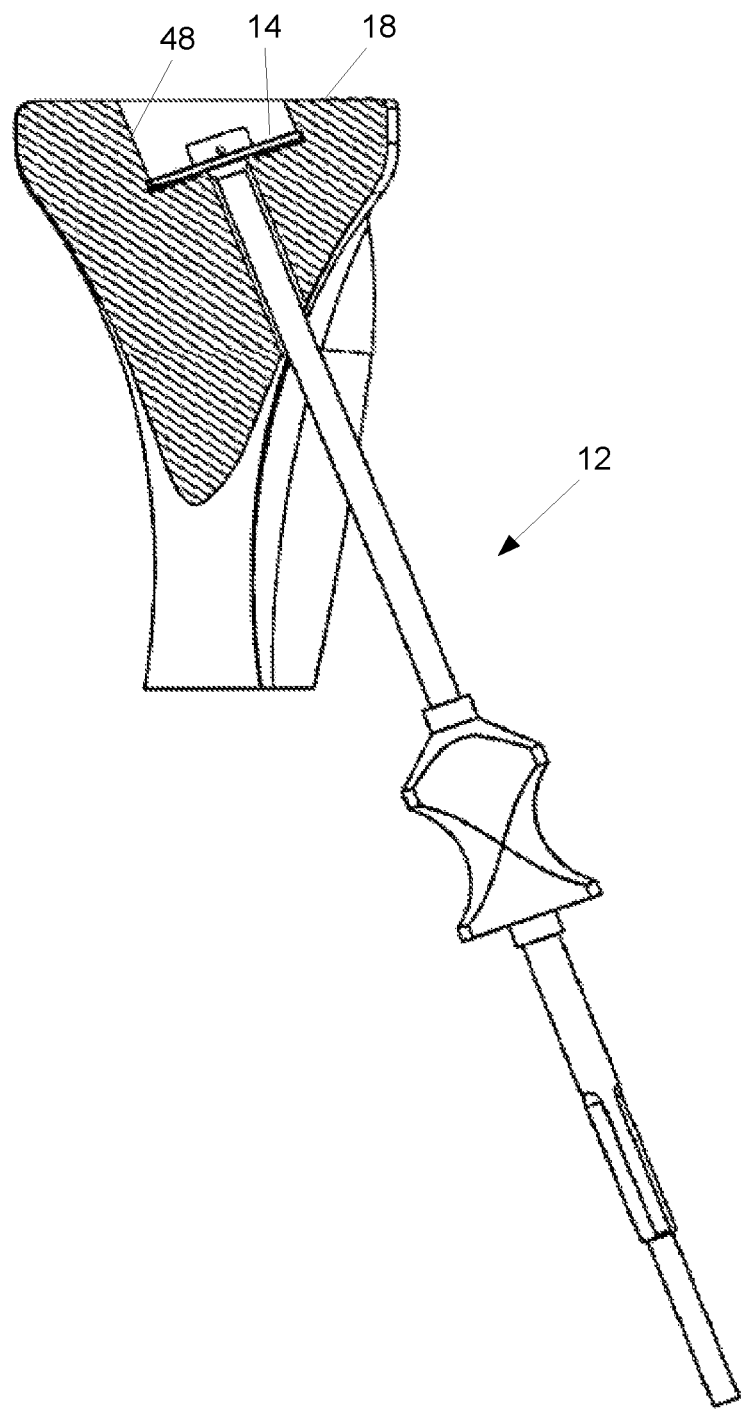
FIG. 8 is a partial cross-sectional view of an implant site formed in the articular surface of a tibia using the retrograde resection apparatus of claim 1.
Figure 9:
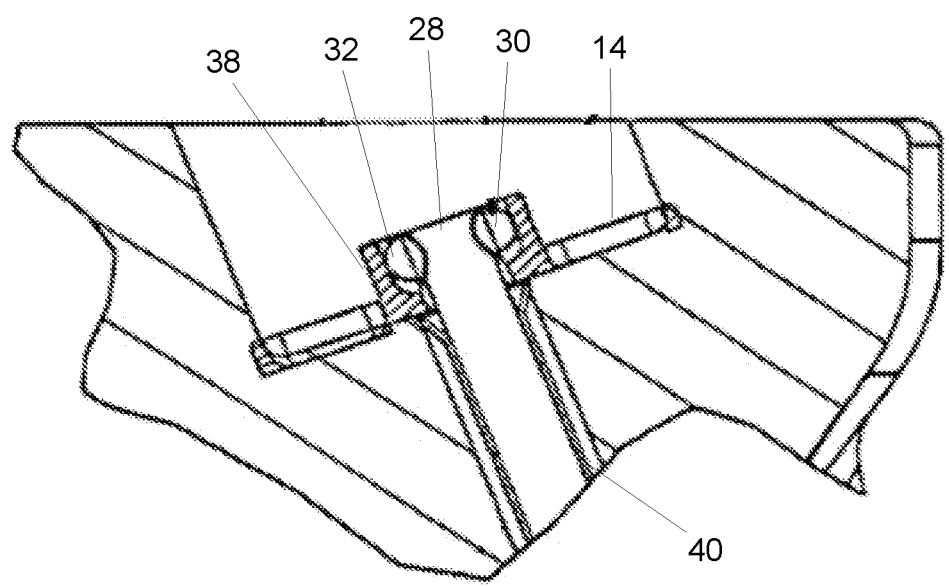
FIG. 9 is a detailed cross-sectional view of the implant site and the retrograde resection apparatus shown in FIG. 8.

Referring also to FIGS. 8 and 9, with the drive component 12 drivingly coupled to the cutting blade 14, an implant site 48 may be formed by resecting at least a portion of the articular surface 18. The cutting blade 14 may be rotatably driven by the drive component 12, which may be driven by a drill or other suitable drive device. As shown, e.g., in FIGS. 6 and 7, the cutting blade 14 may include one or more cutting features 50, 52. The cutting features may include downwardly projecting blades, etc. As the cutting blade 14 is rotatably driven by the drive component 12, the cutting blade 14 and the drive component 12 may be moved in a retrograde direction, urging the cutting blade 14 into the articular surface 18 to resect at least a portion of the articular surface 18 to create the implant site 48. The cutting features 50, 52 may cut, grind, shave, etc., contacted articular cartilage, bone, etc. to create the implant site 48.

With particular reference to FIG. 9, in an embodiment in which the sleeve 40 is urged into engagement with the bottom surface of the cutting blade 14, the cutting blade 14 may be generally oriented perpendicularly to the axis of the drive component 12. Correspondingly, the resected implant site 48 may generally be oriented coaxial with the drive component 12.

Figure 10:
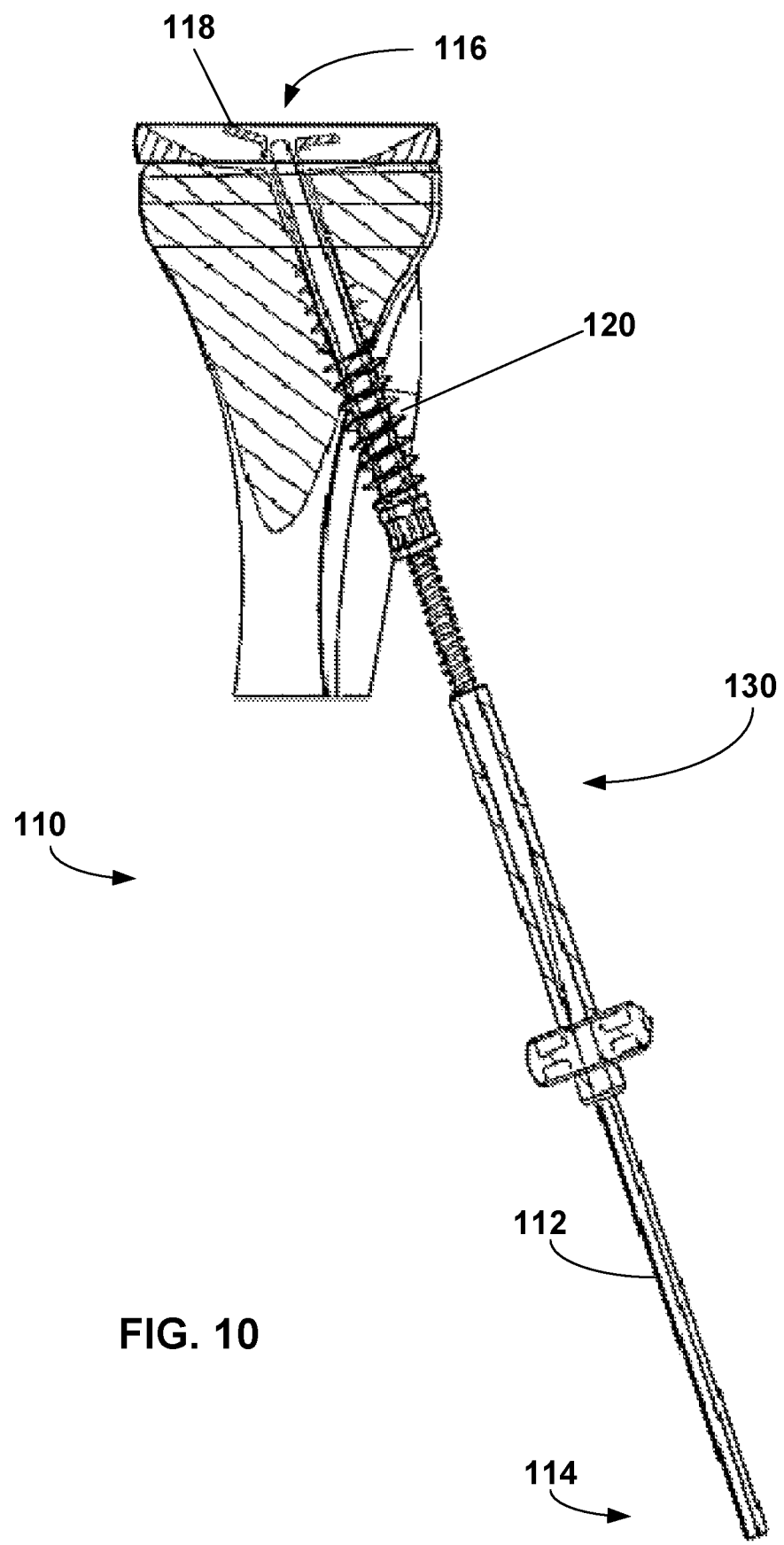
FIG. 10 illustrates a cross-sectional view of an example of a retrograde resection apparatus inserted into a tibia, consistent with the present disclosure.

FIG. 10 illustrates another example of a retrograde resection apparatus 110 contemplated herein. The apparatus 110 includes a drive component, such as an elongate shaft 112, including a proximal portion 114 and a distal portion 116. A cutting blade 118 may be mounted on the distal portion of the shaft 112. A cannulated screw 120 may be provided for receiving the shaft and providing a stopping mechanism for the cutting blade during resection. In addition, a biasing device 130, may be positioned on the shaft 112 to bias the shaft against the screw 120 and/or the cutting blade 118.

Figure 11:
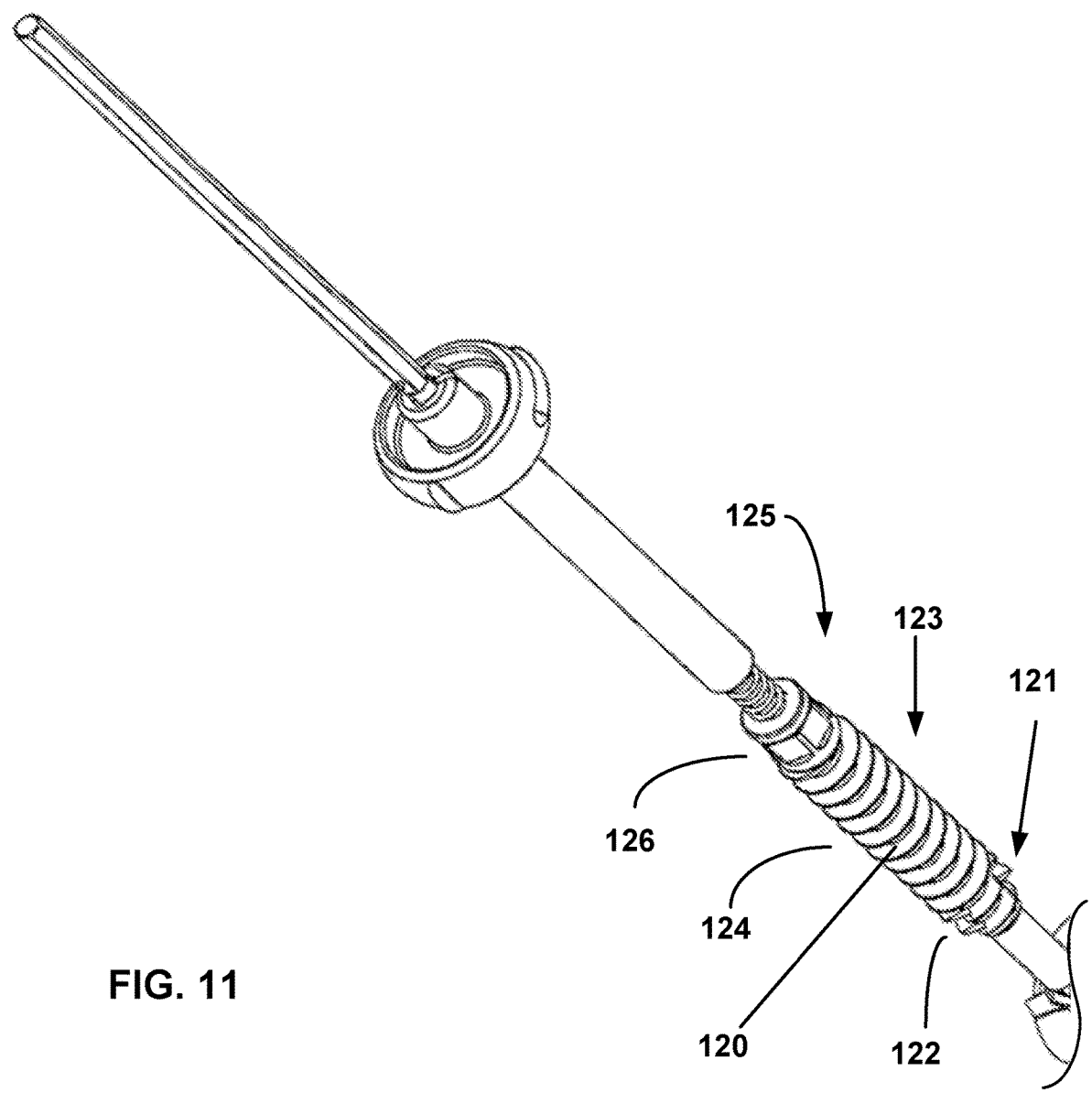
FIG. 11 illustrates a perspective view of an example of a cannulated screw.

As illustrated in FIG. 11, the cannulated screw 120 may include a screw having a bore passing there through. A distal portion 121 of the screw may include a tap 122 or a number of discontinuous threads for cutting threads into the bone. The screw may also include a plurality of continuous threads 124 covering at least a portion of the screw, near the center 123 of the screw. To facilitate turning the screw, a nut 126 may be provided towards the proximal portion 125 of the screw. Thus, in operation, after a retrograde access passage has been formed, one may turn the screw into the bone, tapping the threads and feeding the screw 120, until the screw 120 reaches a desired location or height in the bone proximate to the joint surface. Once the screw 120 is in place, the drive component 112 may be fed through the screw bore and up to the tibia plateau, as illustrated in FIG. 10.

Figure 12:
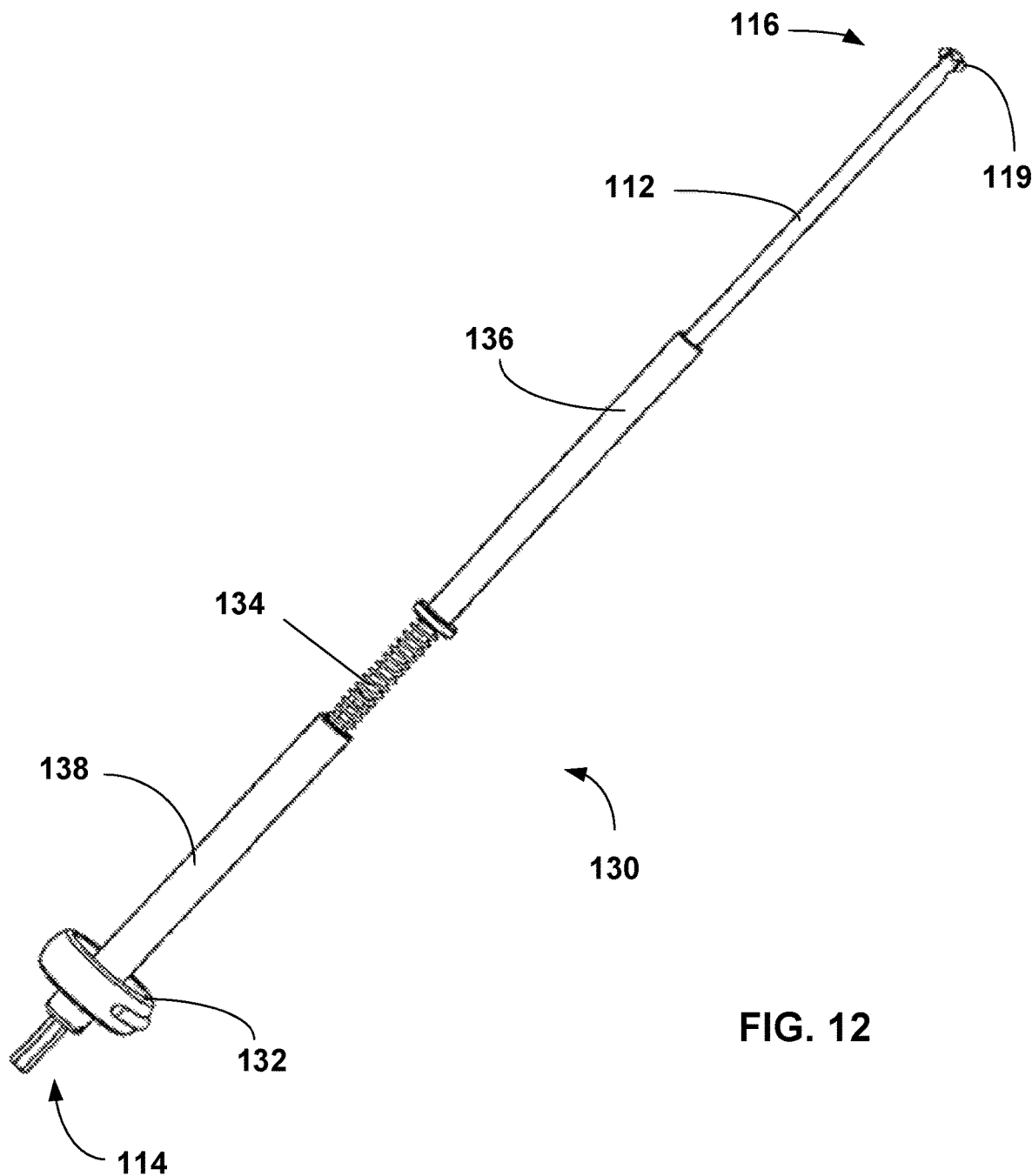
FIG. 12 illustrates a perspective view of an example of a biasing member on a drive component.

The biasing device 130, illustrated in FIG. 12, may include a locking mechanism 132, a spring 134 and one or more sleeves 136, 138, wherein the spring and sleeves may extend between the locking mechanism 132 and the cutting blade 118. The locking mechanism 132 may slidably move up and down the drive component 112 to position the sleeves 136, 138 along the drive component and compress the spring 134. One example of a locking mechanism may include, for example, a bayonet connector, illustrated in FIG. 13. The bayonet connector may include a ring or cylinder 140. The interior surface of the ring or cylinder may include a first channel 142 defined therein along the axis A-A of the drive component 112. This channel may be defined in the entire length of the locking member 132. A stem 144 located on the drive component 112 may pass through the first channel 142 as the locking mechanism 132 is positioned on the drive component 112.

A second notch or channel 146 may be provided in the interior surface of the locking mechanism 132 to receive the stem 144, placing the biasing device 130 in the locked position. The second channel 146 may be defined in only a portion of the locking mechanism 132 surface, i.e., the channel does not pass through the entire length of the locking mechanism 132. In one example, the second channel 146 may include an opening on the proximal side 147 of the locking mechanism and the stem may seat in the second channel. It may be appreciated that this channel may also include a number of other configurations. For example, a first portion of the channel may be defined along axis A-A of the shaft and a second portion may turn at an angle to the first portion. Furthermore, in another example, the channel may include one or more continuous female threads through a portion of the length of the locking mechanism. It may also be appreciated that in other embodiments a channel may be provided, beginning on the distal end 147 of the locking mechanism, for receiving the stem 144.

Figure 13:
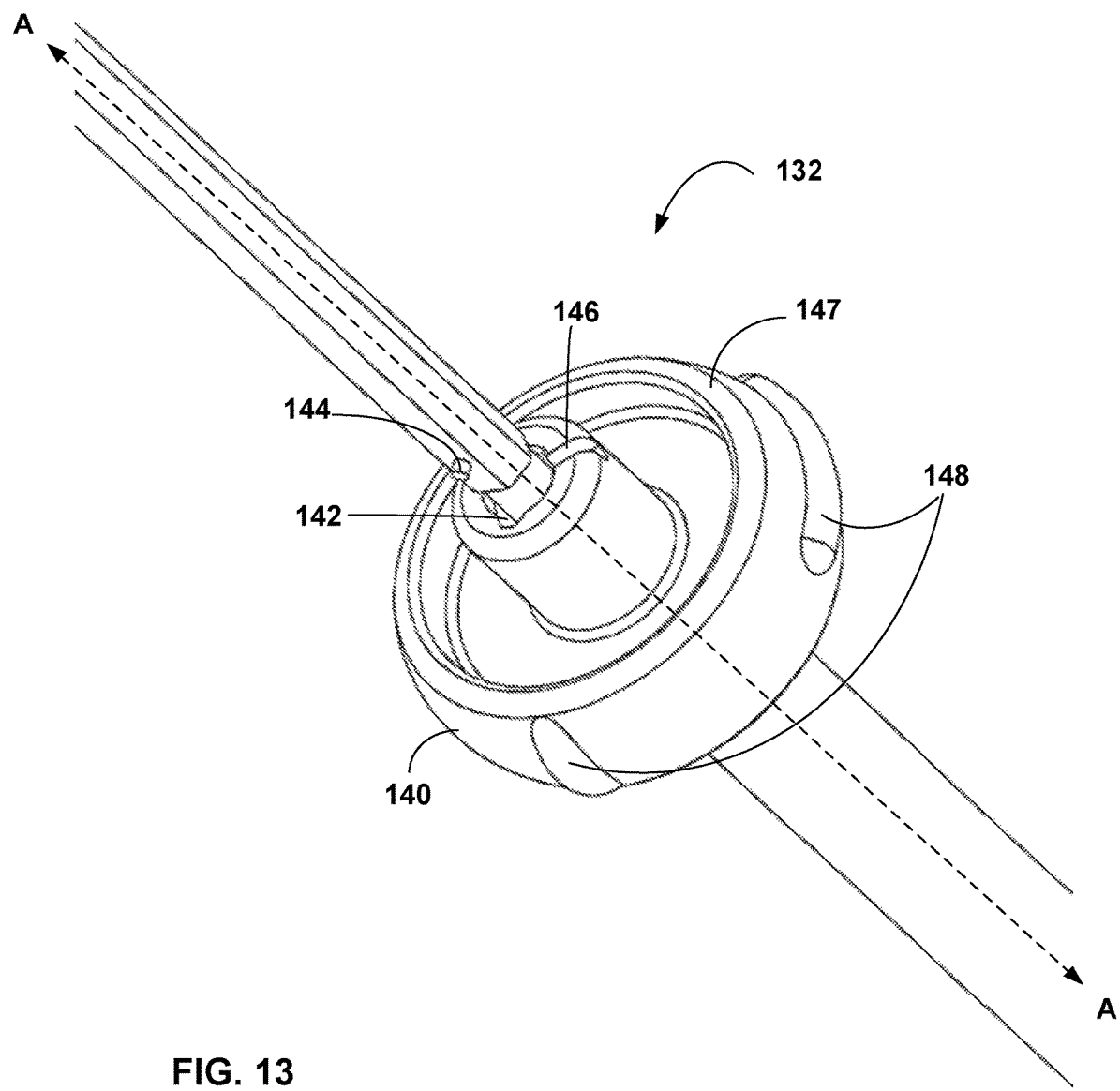
FIG. 13 illustrates a perspective view of an example of a locking mechanism.

While the locking mechanism 132 is illustrated in FIGS. 12 and 13 as being circular in shape, it may be appreciated that the outer diameter of the locking device may be any geometry, such as square, elliptical, rectangular, etc. In addition, the outer surface of the locking mechanism may also include nubs 148 having a raised profile with respect to the remainder of the surface. The nubs 148 may facilitate the user in moving of the locking mechanism about the drive component 112.

Figure 14:
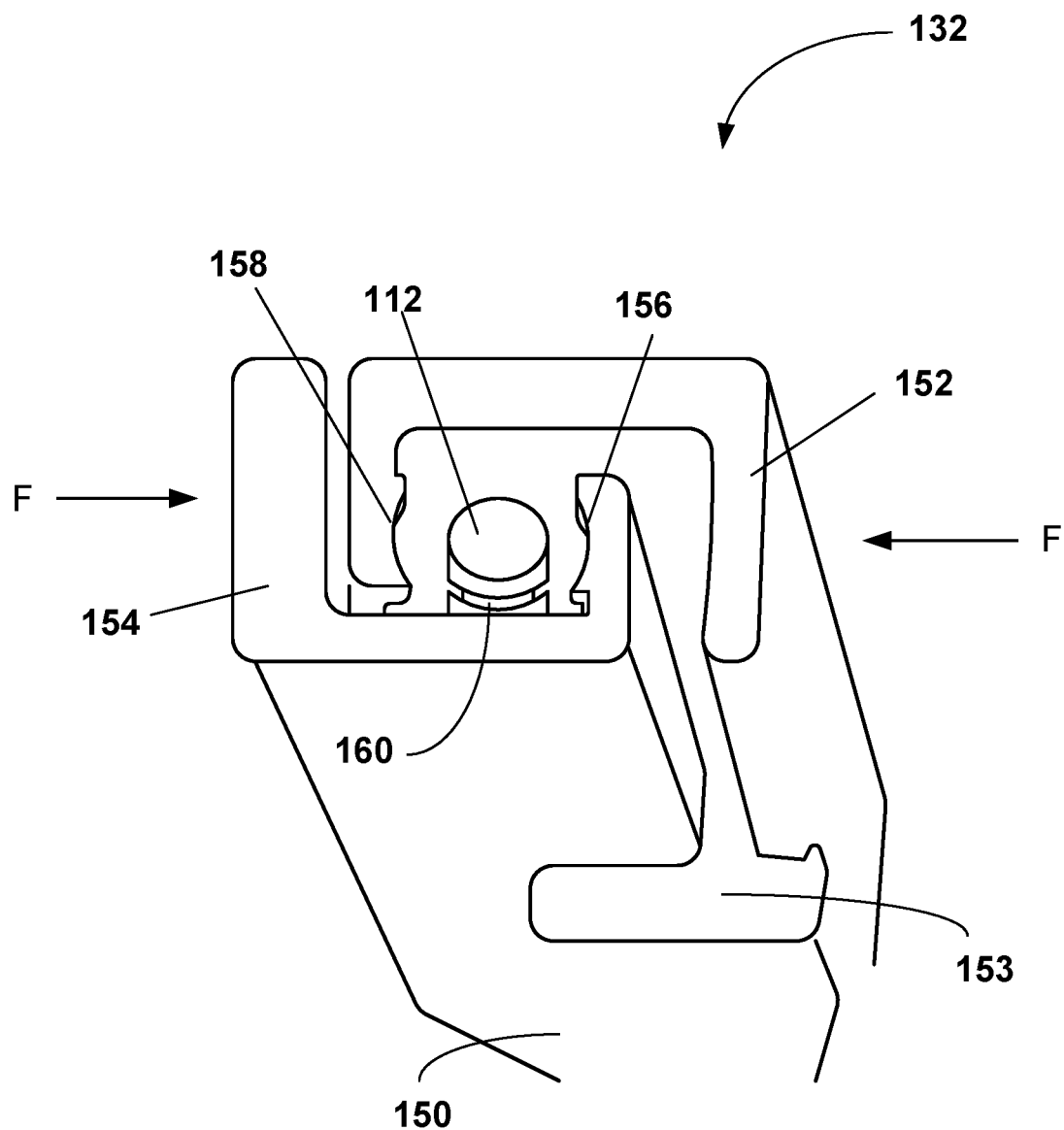
FIG. 14 illustrates a side view of an example of a locking mechanism.
Figure 15:
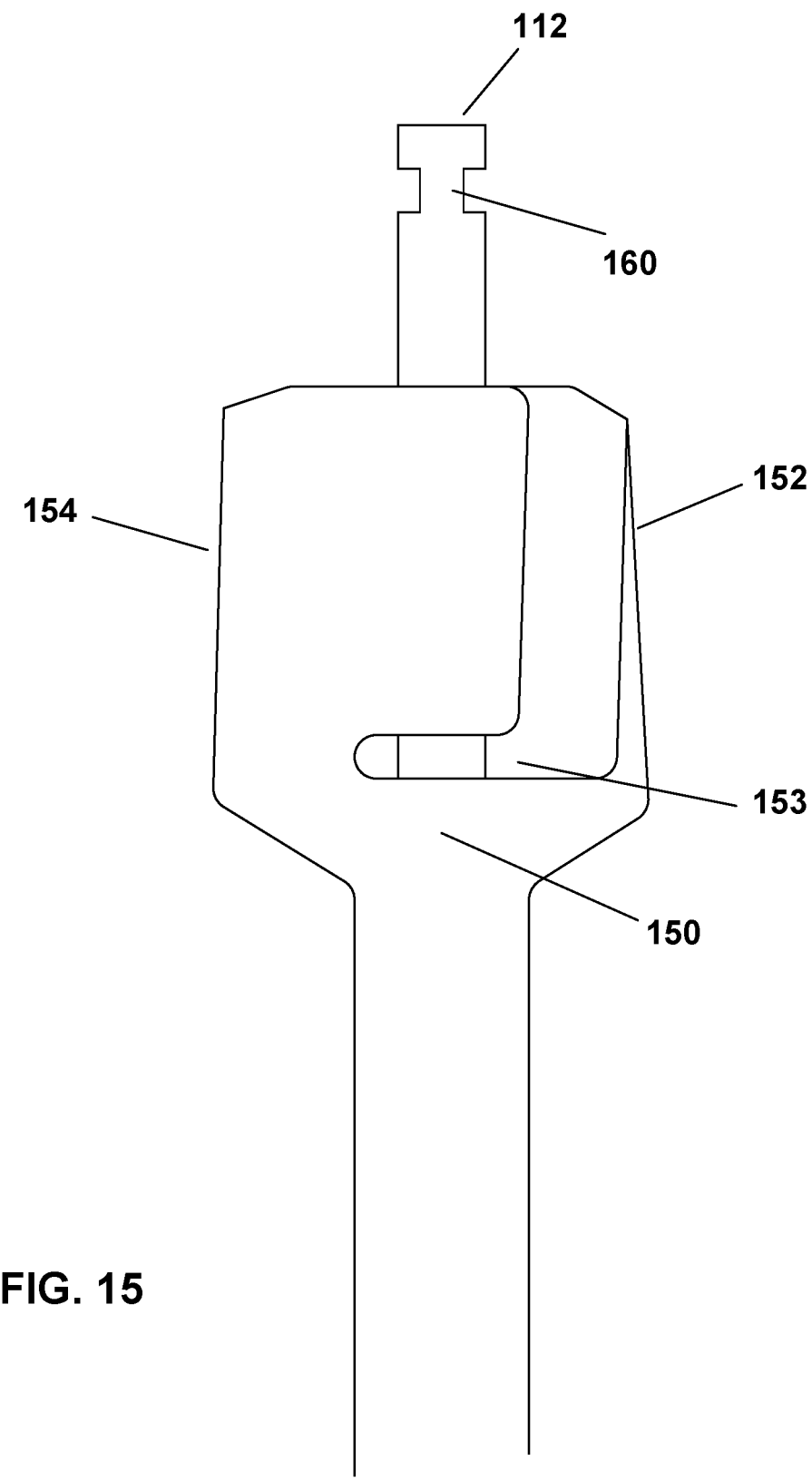
FIG. 15 illustrates a perspective view of the locking mechanism of FIG. 14.

Another example of a locking mechanism 132 is illustrated in FIGS. 14 and 15. The locking mechanism may include a base portion 150 and at least two flexible legs 152, 154 extending from the base portion 150 around the drive component 112. Flexible may be understood herein as capable of being compressed and substantially returning to their original shape. To increase flexibility, a slot 153 may be defined in a portion of the legs proximate to the base The legs may also include a ridge 156, 158, which may be received in recess 160 in the drive component 112. Applying a force F to both sides of the legs 152, 154 may cause the legs to flex inward and away from the drive component 112, removing the ridges 156, 158 from the recess 160 and allowing the locking mechanism to slide up and down the drive component 112.

Referring back to FIG. 12, the biasing device 130 may also include a first sleeve 136, which may be received near the distal end of the drive component 112. The first sleeve may pass through the cannulated screw 120 and abut the bottom surface of the cutting blade 118. A second sleeve 138 may also be provided, which may form a portion of the locking mechanism 132 or may abut the locking mechanism 132. In the present example, a spring 134 may be positioned between the two sleeves 136, 138. The spring may include a stop 135, such as a disc or washer on the distal end, wherein the stop 135 may be received by or abut the nut 126 of the cannulated screw 120. It may be appreciated that the spring 134 may also pass within and be received inside of the second sleeve 138. In addition, it may also be appreciated, that a number of other spring/sleeve combinations may be contemplated, for example one spring and one sleeve may be provided wherein the spring abuts the locking mechanism and the sleeve is positioned between the spring and the cutting blade.

Figure 16:
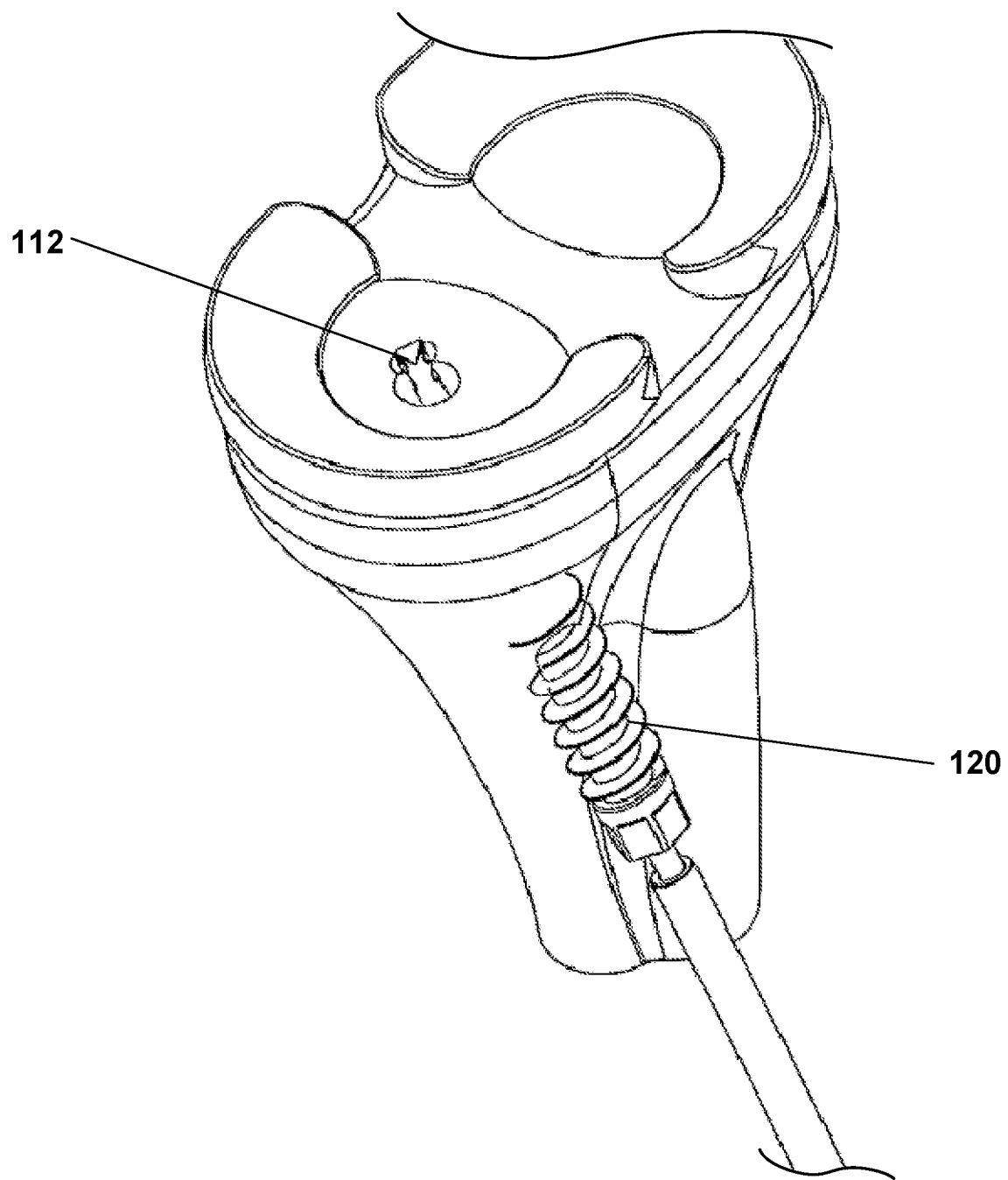
FIG. 16 illustrates a perspective view of the drive component being inserted into the tibia through the cannulated screw and retrograde access passage, consistent with the present disclosure.
Figure 17:
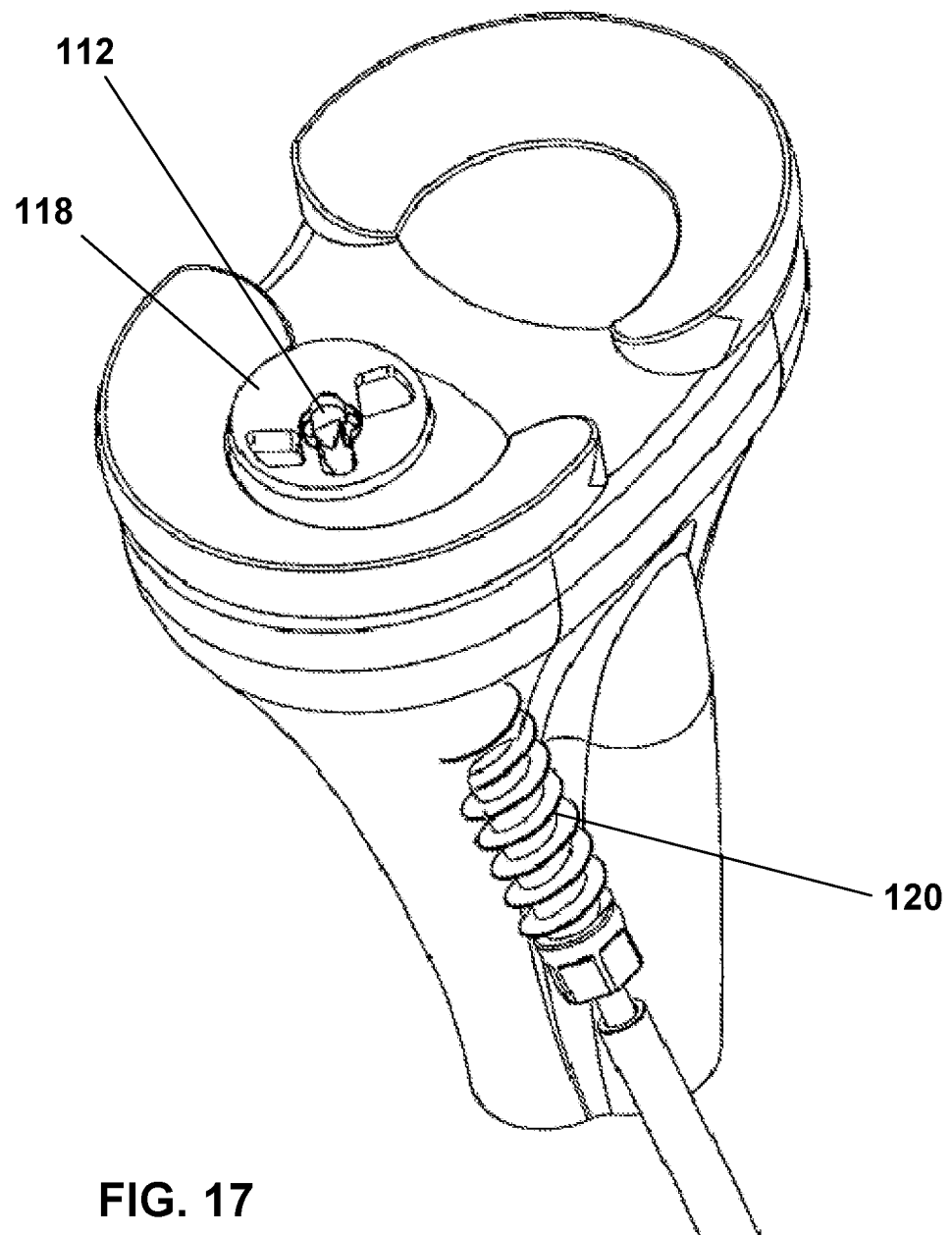
FIG. 17 illustrates a perspective view of the drive component inserted into the tibia mated with a cutting blade.

Accordingly, once the cannulated screw 120 is in place, as described above, one may insert the distal end 116 of the drive component 112 into the resection access passage and through the cannulated screw 120, as illustrated in FIG. 16. The cutting blade 118 may then be fed into the joint proximal to the drive component 112 and positioned on the drive component 112, as illustrated in FIG. 17. It may be appreciated that to position the cutting blade 118, one may use a pair of forceps, dull tweezers or other devices. In addition, one may also attach a tether, such as a suture or thread, to the cutting blade 118 and feed the tether through the resection access path and the cannulated screw 120 bore prior to inserting the drive component 112.

Figure 18A:
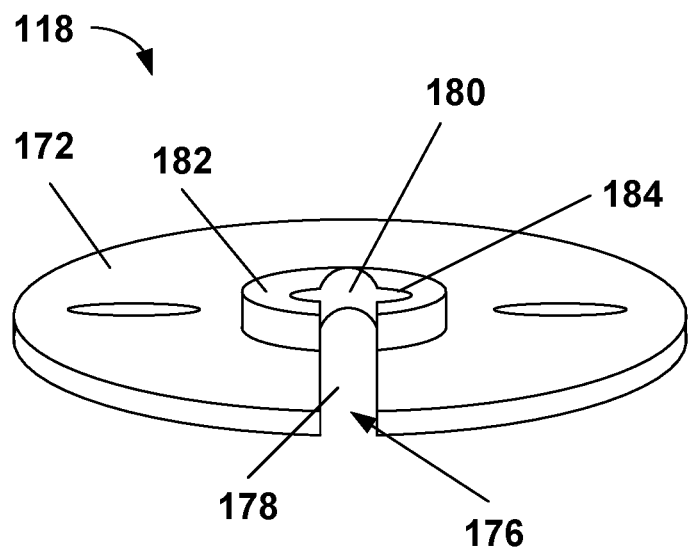
FIG. 18*a*, 18*b*, 18*c* illustrates an example of a cutting blade.
Figure 18B:
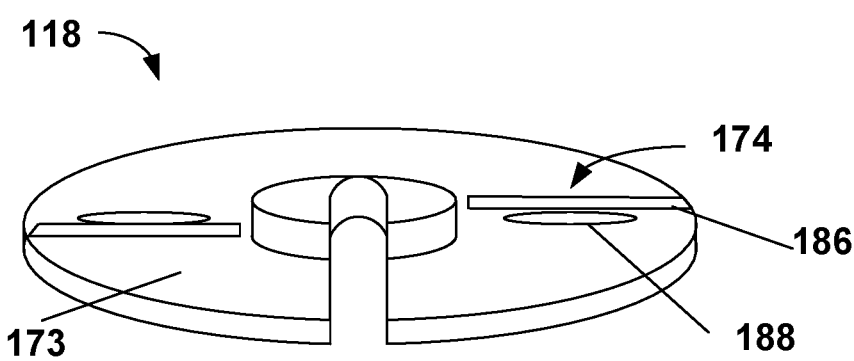
Figure 18C:
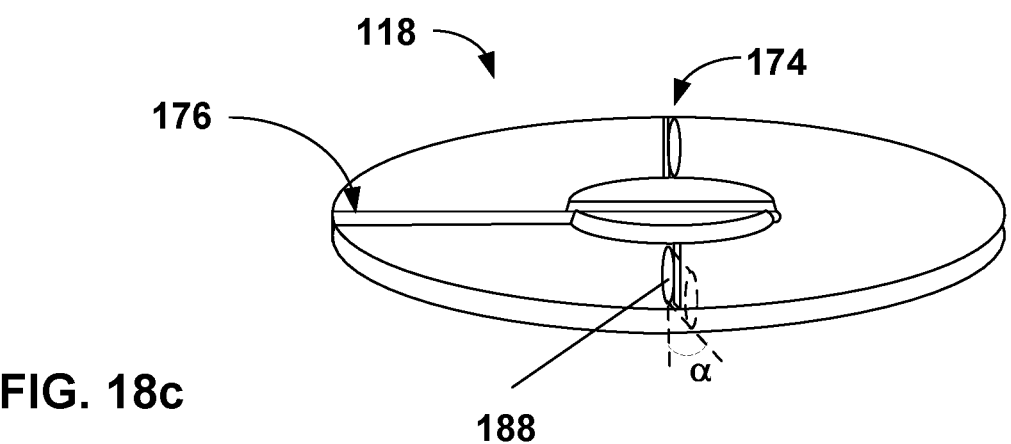

The cutting blade 118, illustrated in FIGS. 18a, 18b and 18c, may include a body 172 having a number of cutting features 174 extending from a bottom surface 173 of the body. The cutting blade 118 may be relatively thin, having a thickness of less than 1 mm, including all values and increments in the range of 1 mm to 0.1 mm. The cutting blade may also include a slot 176 cut through the entire thickness of the cutting device in at least a portion of the cutting blade 118. The slot 176 may have a first portion 178, radially extending from the center of the cutting blade 118 to an edge of the cutting blade. The slot 176 may also have a second portion 180, positioned near the center of the cutting blade 118. The second portion 180 of the slot 176 may be defined in a hub 182, which may extend from the top and/or bottom surface of the cutting device. Defined within the hub 182 and the second portion of the slot 180 may be one or more recesses 184. The recesses 184 may receive the distal portion 116 of the drive component 112 illustrated in FIG. 12. In one example, the drive component 112 may include two hemispherical projections 119, which may slidably be positioned within the recesses 184. In addition, it may be appreciated that the distal portion 116 of the drive component may be sized so as to pass through the slot 176.

The cutting features 174 of the cutting blade 118 may include a lip or blade 186, which projects from the bottom surface of the cutting blade, for removing the bone and any auxiliary tissue. Each cutting feature may also include a slit 188. The slits 188 may pass through the body of the cutting blade at an angle α to the height of the blade, through which debris may pass as resection proceeds.

Figure 19:
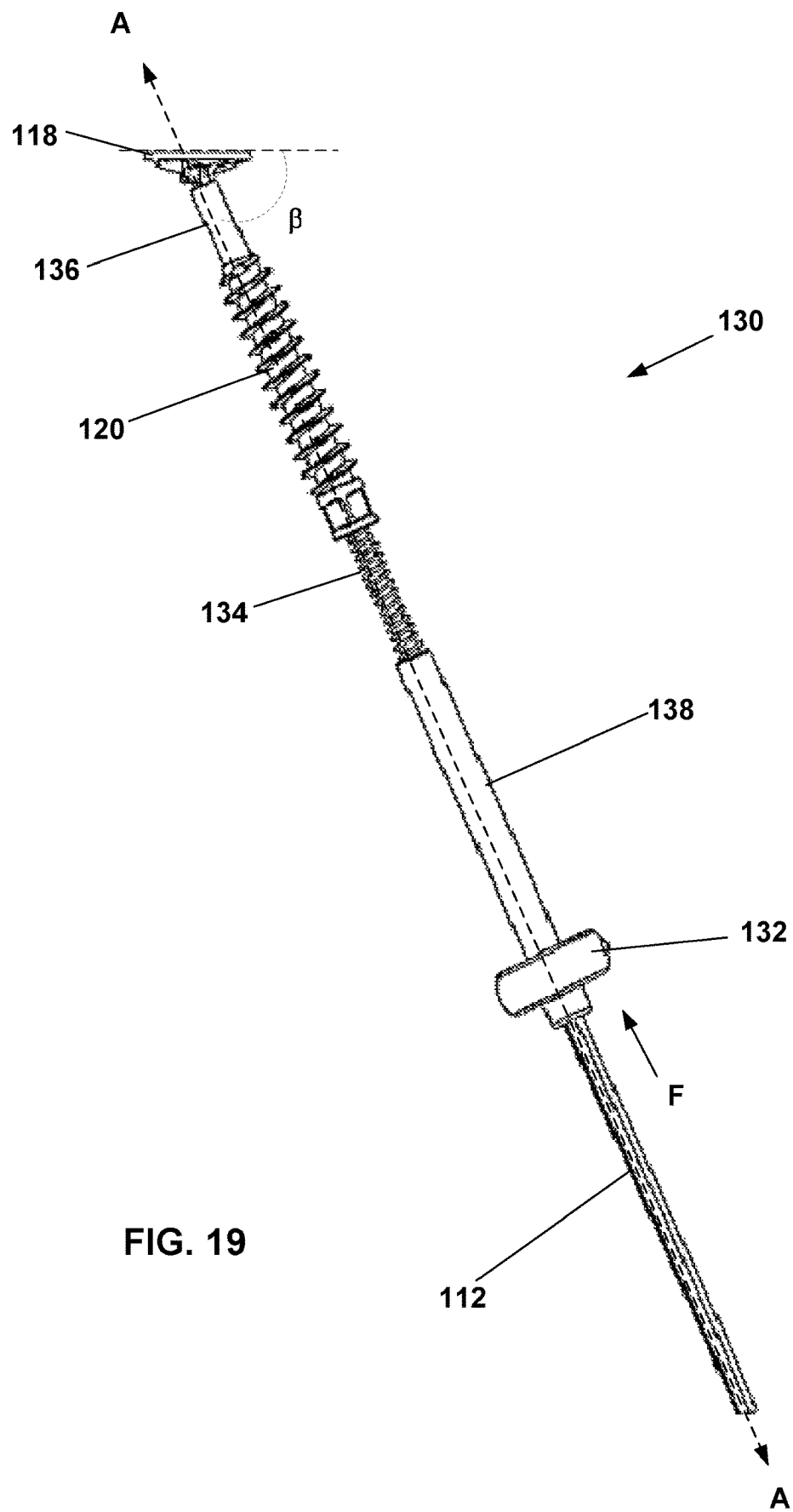
FIG. 19 illustrates a side view of a retrograde resection apparatus in an unbiased or uncompressed state.
Figure 20:
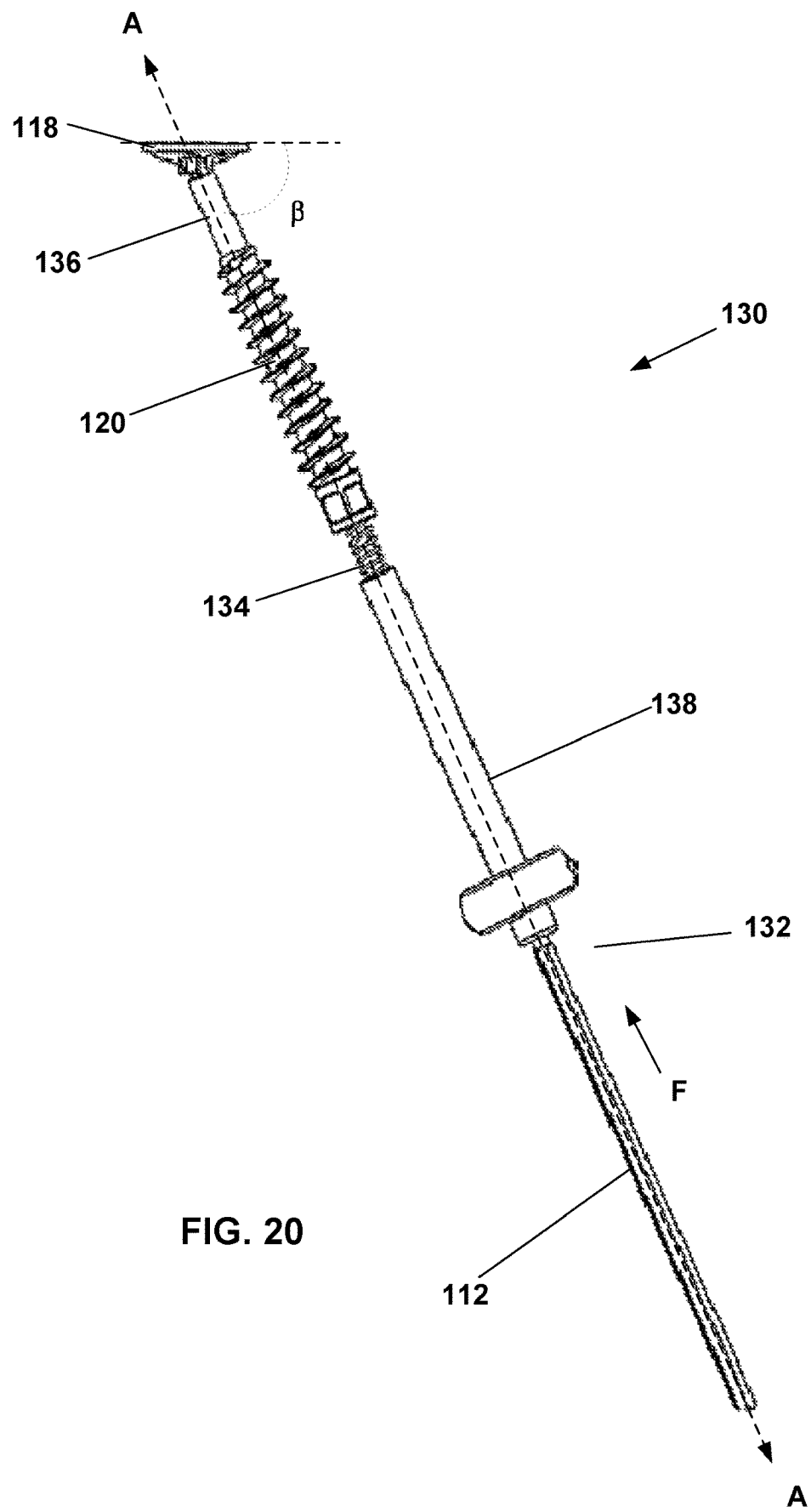
FIG. 20 illustrates a side view of a retrograde resection apparatus in a biased or compressed state.

Once the drive component 112 and cutting blade 118 are mated, the biasing device 130 may be positioned. As illustrated in FIGS. 19 (illustrating the biasing device uncompressed) and 20 (illustrating the biasing device compressed), the first shaft 136 may be arranged within the cannulated screw 120 and abut the cutting blade 118. As force F is applied in the axial direction on the locking mechanism 132 of the biasing device, the spring 134 may compress against the cannulated screw 120 and/or the first shaft 136 as well as the second shaft 138 until the locking member 132 is locked in position.

Once the locking member 132 is locked in position along the drive component 112, a radial force, or torque may be applied to the proximal end of the drive component 112, providing rotation of the cutting device. It may be appreciated that the cutting blade 118, may exhibit polyaxial movement, i.e., the cutting blade may move, not only along the axis of the drive component, but may rotate at an angle β to the drive component as well. For example, the cutting blade 118, may be substantially planar with the tibial plateau and at an angle β in the range of approximately 10 degrees to 80 degrees to the drive component along axis A-A. However, once resection is complete, the angle β of the cutting blade may be in the range of 20 degrees to 90 degrees to the drive component along axis A-A.

Consistent with the foregoing, according to one aspect, the present disclosure may provide a retrograde resection apparatus for creating an implant site in an articular surface of a joint. The retrograde resection apparatus may include a cutting blade and a drive component. The cutting blade may be a disk or wafer and having cutting features extending from, or located on, the bottom surface of the cutting blade. The cutting features may be configured to resect material adjacent to the bottom surface of the cutting blade. The drive component may be configured to be releasably coupled to the cutting blade and may include a shaft for rotatably driving the cutting blade. The cutting blade may include a radial slot sized to receive at least a portion of the shaft of the drive component. The cutting blade may, therefore, be assembled to the shaft of the drive component in situ within the joint by sliding the cutting blade onto the shaft via the slot in the cutting blade. The cutting blade and the drive component may include cooperating features allowing the shaft of the drive component to be coupled to the cutting blade for transmitting torque and axial thrust to the cutting blade. In an embodiment, the cooperating features may include radial protrusions on the shaft and recesses in a hub of the cutting blade configured to at least partially receive the protrusions.

According to another aspect, the present disclosure may provide a method for creating an implant site in an articular surface of a joint. The method may generally include creating a retrograde access passage to the articular surface through bone behind the articular surface. A shaft of a drive component may be inserted though the access passage and a cutting blade may be conveyed to the shaft and may be assembled to the shaft to allow the shaft to rotatably drive the cutting blade and to apply an axial thrust on the cutting blade. The cutting blade may be rotatably driven by the shaft and may be urged into the articular surface. A portion of the articular surface may be resected by cutting features extending from, or located on, the bottom of the cutting blade as the cutting blade is rotated and urged into the articular surface in a retrograde direction.

While the present invention has been set forth above by way of embodiments consistent therewith, the described embodiments are susceptible to numerous modifications and variations without materially departing from the invention. All such modifications and variations are considered to be within the scope of the present invention.

What is claimed is:

1. A retrograde resection apparatus for resecting tissue, comprising:
   a cutting blade having a body defining a first surface a second surface opposite to said first surface, and including at least one cutting feature provided on said second surface;
   a radial slot extending through said first and second surfaces and defined through at least a radial portion of said body;
   a recess defined in said body and located in at least a portion of said radial slot;
   a shaft having a distal end and a proximal end, wherein a portion of said distal end is received in said recess to allow said cutting blade rotatably driven by said shaft;
   a biasing device configured to bias said shaft against said cutting blade; and
   wherein the cutting blade is configured to cut the tissue when the shaft is rotatably driven proximally in a retrograde direction towards the proximal end.

2. The apparatus of claim 1, wherein said portion of said distal end comprises a hemispherical protrusion extending from said distal end of said shaft, wherein said protrusion is configured to be at least partially received in said recess.

3. The apparatus of claim 1, wherein at least a portion of said distal end of said shaft is configured to be received in said slot.

4. The apparatus of claim 1, further comprising a screw, including a proximal end and a distal end defining a bore therethrough, received on said shaft.

5. The apparatus of claim 4, wherein said shaft is rotatable in said bore.

6. The apparatus of 4, wherein said screw includes a nut on said proximal end of said screw.

7. The apparatus of claim 4, wherein said screw includes a plurality of continuous threads in a central portion and a tap proximate said distal end of the screw.

8. The apparatus of claim 1, further comprising:
   a first sleeve slidably positioned on said shaft;
   a spring slidably positioned on said shaft between said first sleeve and said biasing member.

9. The apparatus of claim 1, wherein said shaft includes a stem and said biasing device includes a ring including an interior surface having a channel defined therein for receiving said stem.

10. The apparatus of claim 9, wherein said channel includes a first portion extending along the axis of said shaft and a second portion extending in a direction at an angle from the axis of said shaft.

11. The apparatus of claim 9, wherein said ring comprises a first sleeve extending from said ring, and said apparatus further comprises a spring supported by said first sleeve and a second sleeve positioned between said spring and said cutting blade and upon biasing said ring, said spring is compressed and a force is transmitted to said cutting blade.

12. The apparatus of claim 1, wherein said shaft includes a recess defined therein and said biasing device includes a collar positioned on a portion of said shaft, wherein said collar includes a ridge for being received in said recess defined in said shaft.

13. The apparatus of claim 12, wherein said collar includes a base and flexible legs extending from said base and said ridge is positioned on at least one of said legs and wherein said ridge in a first position is received in said recess defined in said shaft and upon flexing said flexible legs said ridge is configured to be removed from said recess.

14. The apparatus of claim 1, further comprising a tether, wherein said tether is affixed to said cutting blade.

15. The apparatus of claim 1, wherein said cutting blade is non-rotatable with respect to said shaft when said portion of said distal end is received in said recess.

16. The apparatus of claim 1, wherein said cutting blade is tiltable at an angle defined by an axis of said shaft and a surface of said cutting blade.

17. The apparatus of claim 1, wherein said cutting blade body is less than 1 mm in thickness.

18. The apparatus of claim 1, wherein the cutting blade body defines an edge, said cutting blade body has a first thickness and said body tapers to a second thickness proximate to said edge.

19. The apparatus of claim 1, wherein said cutting feature includes a lip extending from said second surface of said body and a slit defined through said body at an angle to the second surface of the cutting device.

20. A retrograde resection apparatus for resecting tissue, comprising:
- a cutting blade having a body defining a first surface and a second surface opposite to said first surface, and including a cutting feature extending from said second surface;
- a radial slot extending through said first and second surfaces and define through a radial portion of said body;
- a recess defined in said body and located in at least a portion of said radial slot;
- a screw, including a proximal end and a distal end defining a bore therethrough;
- a shaft having a distal end and a proximal end, wherein said shaft passes through said bore and a portion of said distal end is configured to be received in said recess to allow said cutting blade rotatably driven by said shaft;
- a biasing member configured to bias said shaft against said cutting blade;
- a tether, a first portion of which is affixed to said cutting blade and a second portion of which passes through said bore; and wherein the cutting blade is configured to cut the tissue when the shaft is rotatably driven proximally in a retrograde direction towards the proximal end.

* * * * *